(12) United States Patent
Biener et al.

(10) Patent No.: US 10,786,642 B2
(45) Date of Patent: Sep. 29, 2020

(54) PATIENT INTERFACE STRUCTURE AND METHOD/TOOL FOR MANUFACTURING SAME

(71) Applicant: ResMed Pty Ltd, Bell Vista, New South Wales (AU)

(72) Inventors: Achim Biener, Aufkirchen (DE); Bernd Christoph Lang, Gräfelfing (DE)

(73) Assignee: ResMed Pty Ltd, Bella Vista, New South Wales (AU)

( * ) Notice: Subject to any disclaimer, the term of this patent is extended or adjusted under 35 U.S.C. 154(b) by 283 days.

(21) Appl. No.: 15/945,532

(22) Filed: Apr. 4, 2018

(65) Prior Publication Data
US 2018/0221612 A1    Aug. 9, 2018

Related U.S. Application Data

(63) Continuation of application No. 12/656,466, filed on Jan. 29, 2010, now abandoned.

(30) Foreign Application Priority Data

Jan. 30, 2009 (EP) ..................... 09001344

(51) Int. Cl.
A61M 16/06    (2006.01)

(52) U.S. Cl.
CPC ........ *A61M 16/06* (2013.01); *A61M 16/0616* (2014.02); *A61M 16/0622* (2014.02); *A61M 16/0633* (2014.02)

(58) Field of Classification Search
CPC .............. A61M 16/06; A61M 16/0605; A61M 16/0611; A61M 16/0616; A61M 16/0622; A61M 2016/0661; A61M 2207/00; A62B 18/00; A62B 18/02; A62B 18/025
See application file for complete search history.

(56) References Cited

U.S. PATENT DOCUMENTS

| | | |
|---|---|---|
| 443,191 A | 12/1890 | Illing |
| 781,516 A | 1/1905 | Guthrie, Jr. |
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |

(Continued)

FOREIGN PATENT DOCUMENTS

| | | |
|---|---|---|
| AU | 199651130 | 10/1996 |
| AU | 2005100738 | 11/2005 |

(Continued)

OTHER PUBLICATIONS

U.S. Appl. No. 10/385,701, filed Aug. 2003, Berthon-Jones et al.

(Continued)

*Primary Examiner* — Joseph D. Boecker
(74) *Attorney, Agent, or Firm* — Nixon & Vanderhye P.C.

(57) ABSTRACT

Component of a patient interface, particularly a cushion, comprising a first part and a second part, wherein the second part is made of a foamed material which is foamed-on the first part. A Method and tool for manufacturing a component of a patient interface, particularly a cushion, comprising the steps molding a first part of the component and foaming a second part on the first part.

33 Claims, 9 Drawing Sheets

(56) References Cited

U.S. PATENT DOCUMENTS

| | | |
|---|---|---|
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,670,726 A | 3/1972 | Mahon et al. |
| 3,682,171 A | 8/1972 | Dali et al. |
| 3,739,774 A | 6/1973 | Gregory |
| 3,754,552 A | 8/1973 | King |
| 3,848,925 A | 11/1974 | Harder |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 11/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 11/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 11/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,304,146 A | 4/1994 | Johnson et al. |
| 5,299,599 A | 5/1994 | Farmer et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,526,806 A | 1/1996 | Sansoni |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,533,506 A | 7/1996 | Wood |
| 5,538,000 A | 7/1996 | Rudolph |
| 5,538,001 A | 7/1996 | Bridges |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |
| 5,655,527 A | 8/1997 | Scarberry et al. |
| 5,662,101 A * | 9/1997 | Ogden .................. A61M 16/06 |
| | | 128/202.27 |
| 5,682,881 A | 11/1997 | Winthrop et al. |
| 5,704,345 A | 1/1998 | Berthon-Jones et al. |

(56) References Cited

U.S. PATENT DOCUMENTS

| | | |
|---|---|---|
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielson |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 1/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,523,754 B2 | 4/2009 | Lithgow |
| 7,658,189 B2 | 2/2010 | Davidson |
| 8,701,667 B1 | 4/2014 | Ho et al. |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | DeVoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0196656 A1 | 10/2003 | Moore et al. |

(56) References Cited

U.S. PATENT DOCUMENTS

| | | |
|---|---|---|
| 2003/0196658 A1 | 10/2003 | Ging et al. |
| 2003/0217746 A1 | 11/2003 | Gradon et al. |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0211428 A1 | 10/2004 | Jones |
| 2004/0226564 A1 | 11/2004 | Persson |
| 2004/0226566 A1 | 11/2004 | Gunaratnam |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0150495 A1 | 7/2005 | Rittner et al. |
| 2005/0155604 A1 | 7/2005 | Ging et al. |
| 2005/0199239 A1* | 9/2005 | Lang ............ A61M 16/06 128/206.24 |
| 2005/0211252 A1 | 9/2005 | Lang et al. |
| 2005/0241644 A1 | 11/2005 | Gunaratnam |
| 2005/0284481 A1 | 12/2005 | Meyer |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1* | 6/2006 | Berthon-Jones ...... A61M 16/06 128/206.21 |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1 | 10/2006 | Davidson et al. |
| 2006/0283461 A1 | 12/2006 | Lubke et al. |
| 2007/0023044 A1 | 2/2007 | Kwok et al. |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0041388 A1* | 2/2008 | McAuley ............ A61M 16/06 128/206.24 |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0149104 A1* | 6/2008 | Eifler ............ A61M 16/06 128/206.24 |
| 2008/0200880 A1 | 8/2008 | Kyvik et al. |
| 2008/0257354 A1* | 10/2008 | Davidson ............ A61M 16/06 128/206.24 |
| 2008/0302365 A1* | 12/2008 | Cohen ............ A61M 16/06 128/206.12 |
| 2009/0014007 A1 | 1/2009 | Brambilla et al. |
| 2009/0044808 A1 | 2/2009 | Guney et al. |
| 2010/0000534 A1 | 1/2010 | Kooij et al. |
| 2010/0018534 A1 | 1/2010 | Veliss et al. |
| 2010/0192955 A1 | 8/2010 | Biener et al. |
| 2011/0088699 A1* | 4/2011 | Skipper ............ A61M 16/0638 128/206.26 |
| 2011/0146684 A1* | 6/2011 | Wells ............ A61M 16/06 128/205.25 |

FOREIGN PATENT DOCUMENTS

| | | |
|---|---|---|
| DE | 185017 | 5/1907 |
| DE | 30 11 900 | 10/1980 |
| DE | 146 688 | 2/1981 |
| DE | 37 19 009 | 12/1988 |
| DE | 39 27 038 | 2/1991 |
| DE | 297 23 101 | 7/1998 |
| DE | 197 03 526 | 8/1998 |
| DE | 199 44 242 | 3/2001 |
| DE | 100 02 571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 | 11/2002 |
| EP | 1 481 702 | 12/2004 |
| FR | 2 720 280 | 12/1995 |
| GB | 532214 | 1/1941 |
| GB | 2 176 404 | 12/1986 |
| GB | 2 368 533 | 5/2002 |
| GB | 2 385 533 | 8/2003 |
| WO | WO 1982/003548 | 10/1982 |
| WO | WO 1987/001950 | 4/1987 |
| WO | WO 1992/020392 | 11/1992 |
| WO | WO 1992/020395 | 11/1992 |
| WO | WO 1996/028207 | 9/1996 |
| WO | WO 1998/004310 | 2/1998 |
| WO | WO 1998/012965 | 4/1998 |
| WO | WO 1998/023305 | 6/1998 |
| WO | WO 1999/016327 | 4/1999 |
| WO | WO 1999/025410 | 5/1999 |
| WO | WO 1999/043375 | 9/1999 |
| WO | WO 1999/061088 | 12/1999 |
| WO | WO 2000/020072 | 4/2000 |
| WO | WO 2000/038772 | 7/2000 |
| WO | WO 2000/050121 | 8/2000 |
| WO | WO 2000/069521 | 11/2000 |
| WO | WO 2000/072905 | 12/2000 |
| WO | WO 2000/074758 | 12/2000 |
| WO | WO 2000/076568 | 12/2000 |
| WO | WO 2000/078384 | 12/2000 |
| WO | WO 2001/062326 | 8/2001 |
| WO | WO 2001/095965 | 12/2001 |
| WO | WO 2001/097892 | 12/2001 |
| WO | WO 2001/097893 | 12/2001 |
| WO | WO 2002/038221 | 5/2002 |
| WO | WO 2002/045784 | 6/2002 |
| WO | WO 2003/090827 | 11/2003 |
| WO | WO 2003/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063328 | 7/2005 |
| WO | WO 2005/076874 | 8/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |

(56) References Cited

FOREIGN PATENT DOCUMENTS

| WO | PCT/AU2007/001936 | 12/2007 |
|---|---|---|
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |
| WO | WO 2010/148453 A1 | 12/2010 |

OTHER PUBLICATIONS

U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Communication issued in a corresponding European Application No. 09 001 344.2 dated Oct. 4, 2012.
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, dated Dec. 1, 2009.
Examination Report filed in New Zealand Application 539836, dated Aug. 25, 2005.
Examiner's Report No. 3 dated Nov. 18, 2009 in New Zealand Application No. 2003275762.
Extended European Search Report dated Mar. 19, 2009 in European Application No. EP 08161249.
Extended European Search Report dated Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action dated Dec. 22, 2009 in European Appln. No. 04802133.1.
ResMed Co.—Mask Products13 http://resmed.com/portal/site/ResMedUS/index.jsp.
Respironics Co.—Mask Family—http://masksfamily.respironics.com.
Snapp Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report dated Sep. 8, 2009 in European Appln. No. 04802133.1.
Supplementary Search Report issued in European Appln. 05746824.1, dated Dec. 17, 2009.
Supplementary European Search Report dated Dec. 18, 2009 in European Application No. 03810331.3.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.

(56) References Cited

OTHER PUBLICATIONS

International Search Report PCT/AU2009/001144, dated Dec. 18, 2009.

* cited by examiner

PATIENT INTERFACE STRUCTURE AND METHOD/TOOL FOR MANUFACTURING SAME

This application is a continuation of U.S. patent application Ser. No. 12/656,466, filed Jan. 29, 2010, now abandoned, which claimed priority to European Patent Application No. 09001344.2, filed Jan. 30, 20109, the entire contents of each of which are hereby incorporated herein by reference in their entirety.

The invention relates to patient interfaces such as breathing masks covering nose and/or mouth of a patient and components or structures thereof as well as to methods for manufacturing such patient interfaces or components thereof and further relates to tools for manufacturing the same. Furthermore, the present invention relates to cushions, pads, supporting structures and/or sealing structures, such as mask cushions or forehead pads etc. for a patient interface such as a breathing mask. Moreover, the present invention relates to a patient interface or component of a patient interface obtainable by a method according to the present invention as well as to a tool for producing such interface or component and/or for performing a respective method.

The invention concerns, in particular, a pad or cushion and a patient interface such as a breathing mask which is equipped with such pad or cushion. An internal space of a breathing mask is established by the patient interface in conjunction with sealing contact of the pad or cushion with the surface of the face of a user. This internal space is sealed in relation to the ambient atmosphere in such a way that a pressure which is preferably increased in relation to the ambient pressure can be obtained, e.g. in phase-wise fashion, in the internal space of the patient interface or breathing mask. Breathing masks of that kind are used in particular in connection with the medical or therapeutic administration of breathable gases and also in the technical sector, for example in the sector of breathing apparatus technology, and particularly for CPAP and BiPAP therapy. The invention further concerns a sealing, contact and/or support structure and a process and tool for the production thereof in general.

Usually, with such patient interfaces, the sealing action in relation to the surface of the face of the user of the interface is achieved by a sealing lip structure. Such sealing lip structure, e.g., extends in inwardly directed relationship around an opening of the mask, and is made from an elastically deformable material.

The sealing action achieved with sealing lips of that kind generally increases with the pressure with which the sealing lip is pressed against the surface of the face. In the case of comparatively high contact pressures, in particular long-term use of breathing masks of that kind can give rise to troubles.

Patient interfaces and patient interface structures or components, e.g., sealing lips, are known in the prior art, for example, in the field of face masks for delivering breathable air to a patient. In such face masks, often hollow cushions or bent, resilient lip-structures are used for providing contact zones for contacting the face of the user in order to avoid dents and to improve wearing comfort of the user. Furthermore, such structures are used as a sealing structure for sealing the mask interior from the exterior in the contact region where the mask rests on a user's face.

A disadvantage of structures known in the art is that they are complicated to manufacture and a number of manual manufacturing steps is often necessary. Often a number of different parts is manufactured wherein the parts are provided with connection structures and have to be assembled to form the final product.

For examples, breathing masks are known which comprise an individually molded part made of polyurethane foam which is loosely fitted into the mask frame for constituting part of a face mask cushion. However, this kind of assembly requires providing structures in the mask seal, the mask body or both that allow for a mechanical linkage between these at least two components. This typically requires the use of additional materials to form different parts of a mask structure, increases the complexity of the design as well as the manufacture of the mask. This leads to limitations in design due to the requirements of providing connection structures, and requires a complex hand assembly or hand manipulation for assembling the mask etc.

The solutions known in the prior art are in particular, not easy to handle, not durable, complicated and expensive to manufacture, not suitable for automating, not bio-compatible as well as optically and hygienically objectionable. The known solutions are further disadvantageous in that they do not or insufficiently allow individualization and are less comfortable for a wearer, particularly with regard to material properties such as weight and hardness.

WO 2007/009182A1 refers to a respiratory mask and a method for manufacturing a respiratory mask comprising a first component formed from a material that is more rigid than the flexible material, wherein the first component is formed onto the second component by an over molding process.

WO 03/105921A2 relates to a mask cushioning and forehead pad for a respiratory mask, and a method for its production comprising a mask cushioning having zones with an increased cross-section that are configured in the mask cushioning, wherein the mask cushioning material in said zones has different material properties in such a way that the Shore hardness of the mask cushioning in the boarder region is higher than in the core region. Although, this disclosure is advantageous in that it provides a one piece hygienic component, it still suffers from the above disadvantageous, particularly from limitations in the design of the sealing structures and from complex manufacturing methods.

It is an object underlying the present invention to provide a patient interface or a component of a patient interface, such as a cushion or pad, a method for manufacturing such patient interface and/or component as well as a tool for manufacturing the same which overcome the deficiencies of the prior art. Alternatively or additionally, it is an object underlying the present invention to provide a patient interface or component thereof which has an improved sealing effect and/or an improved level of wearing comfort. Alternatively or additionally, it is an object underlying the present invention to provide a method for manufacturing a patient interface or component thereof and/or a tool for manufacturing the same which allows efficient and effective production and handling of improved patient interfaces and/or components thereof.

These objects are fulfilled with the features of the claims wherein dependent claims relate to preferred features of the present invention.

The present invention relates to a patient interface structure or component, e.g., a breathing mask and components thereof. Such components are, e.g., a pad or a cushion for supporting and/or sealingly supporting a breathing mask or patient interface on a user's skin. Moreover, the present invention relates to a method and tool for manufacturing a patient interface or patient interface component, particularly those according to the present invention.

According to the present invention, a component of a patient interface, such as a face mask, and in particular a patient interface cushion comprises a first part and a second part, wherein the second part is made of a foamed material which is foamed-on the first part. The first and second parts are preferably parallelly and/or subsequently co-molded. Preferably, the first and second part have a different hardness wherein the first part is molded in a first step and wherein the second part is subsequently molded-on or foamed-on the first part. Preferably, the first part is made of a hard material, particularly with regard to the second material, and the second material is made of a soft material, particularly with regard to the first material. Preferably, the first material is harder than the second material.

Preferably, foaming-on of the second part to the first part and the co-molding of the first part and the second part results in the first and second part being formed integrally with one another.

The method and tool according to present invention particularly allow to mold a foamed part on or onto another part in an easy, reliable, efficient and effective manner. In particular, the present invention does not require that a component of a first part and a foamed second part are formed by 'surrounding' the first part by a foamed material wherein the first part constitutes a core. Preferably, there is no positive locking or form closure needed for foaming or molding the second material to the first material.

According to a further alternative or additional aspect, the present invention relates to a component of a patient interface, such as a breathing mask, and in particular to a patient interface cushion comprising a support structure, such as a frame-component and a cushion or undercushion for supporting the interface on a patient's face. Preferably, the component further comprises a membrane, particularly for sealing the cushion against a users face.

According to a preferred aspect of the present invention, the first part and the second part integrally merge at a merging or contact surface constituting the contact area between said two parts. Said merging surface preferably is a substantially plane surface and/or a surface having a substantially plane cross-section. Preferably, the merging or contact surface comprises at least two distinct surface portions. Preferably, the merging or contact surface comprises a first surface portion and the second surface portion wherein the first surface portion and the second surface portion are inclined towards one another.

Preferably, the merging or contact surface has a plane, an elbow-shaped, U-shaped, recessed, cup-like, and/or hook-shaped profile at least at a part of its cross-section. Preferably, the merging or contact surface does not have undercuts. Also preferably, the first portion and second portion solely merge via such merging surface and/or are not connected by means of structural or mechanical fastening means. Preferably, the contact surface of the first material comprises bores and/or cavities which are at least partly filled by the second material when foaming the second material on the first material.

According to a preferred embodiment, the component of a patient interface according to the present invention is a breathing mask cushion for sealingly supporting a breathing mask on a wearer's face, a forehead pad for supporting a breathing mask on a wearer's face, part of a headband for securing a device such as a breathing mask to a wearer's head or other parts or components for contacting a wearer's body.

Preferably, such interface comprises a thin membrane for sealingly contacting a user's skin and an undercushion being thicker than the membrane and being arranged—when viewed from the patient—under or behind said membrane. Preferably, the second part according to the present invention constitutes such undercushion wherein the first part is adapted to support the second portion and to connect it to a patient interface frame. Preferably, the first part also comprises the membrane being integrally formed therewith or being, preferably releasably, attached thereto.

Thus, preferably, the membrane forms an outer portion of the patient interface (cushion) for, preferably sealingly, contacting a wearer's skin wherein the second part or undercushion is shielded vis-à-vis the wearer's skin by the membrane and is attached, preferably releasably, to the patient interface by means of the first part. Thus, the second part preferably does not directly contact the wearer's skin.

Preferably, a patient interface component, here e.g. a mask cushion, comprises a membrane or sealing lip portion and a cushion or undercushion comprising a connection portion for connecting it to a mask frame. The membrane or sealing lip portion is preferably an independent, non-integral part which is individually connected to the mask frame. According to an alternative preferred embodiment, the membrane or sealing lip portion is co-molded and integrally formed with support portions of the patient interface, such as, e.g., the mask frame and/or the first part according to the preset invention. The mask cushion or undercushion comprises a cushion portion and a connection portion. Preferably, the connection portion corresponds to the first part as referred to herein wherein the cushion portion corresponds to the second part as referred to herein. The connecting portion or the first part and the cushion portion or second part of the component, respectively, form a merging surface or contact area along which the first and second part merge. The second part is made of a foam or a foamed material. Preferably, the second part is co-molded to or foamed-on the first part along the contact area or merging surface.

The component according to the invention preferably forms an undercushion of a breathing mask cushion which is shielded or covered vis-à-vis a wearer by a membrane or sealing lip portion which at least partially extends along and over undercushion portion, respectively, when assembled to a mask frame.

Preferably, the second part is located in the mask interior oriented or facing towards the outside environment of the mask or towards a wearer, respectively whereas the first part of the mask cushion is located in the mask interior oriented or facing towards the inside of the mask or away from a wearer, respectively.

Preferably, the first part is not or does not comprise a foam or foamed material wherein the second part is made of or comprises a foamed material. Preferably, the first part has a first material characteristic and the second part has a second material characteristic different from the first material characteristic. Preferably, said characteristic is hardness. Preferably, the (first) hardness of the first part is higher than the (second) hardness of the second part.

Preferred materials are resilient or elastic materials allowing application of different hardnesses. According to a preferred embodiment, the first part comprises a polymer, e.g., a polysiloxane; silicone; liquid silicone rubber, and/or thermoplastic elastomer. According to a preferred embodiment, the second part comprises foamed materials, e.g., foamed silicone and/or foamed polyurethane. Preferably, the second part is made of a material having visco-elastic properties.

The breathing mask cushion and patient interface, respectively, preferably comprises a longitudinal axis extending generally perpendicular to a contact plane in which the cushion or interface substantially contacts a wearer. Preferably, at least a portion of the contact region or merging surface between the first part and the second part is parallel with regard to said axis and/or said contact plane in which the cushion or interface substantially contacts a wearer. Preferably, the contact region comprises one or more, at least two and preferably three distinct portions. According to a preferred embodiment the contact region is directed towards one side of the first/second part only. Preferably, the second part does not surround or include the first part or portions thereof. Preferably, the contact region, the first part and/or the second part are generally ring shaped. The ring can be closed or can be open, i.e. a ring-segment. The method and tool according to the present invention particularly allow to foam the second part on the first part from one side only and onto substantially plane surfaces, generally to any surface of the first part.

In addition or alternatively, the present invention relates to a method for producing a component of a patient interface or a patient interface, respectively. In particular, the method according to the present invention relates to the production of a patient interface or component of a patient interface, such as a breathing mask cushion, as discussed and disclosed in the present application. A preferred method according to the present invention comprises the steps of providing a molding tool having a first mold part and a second mold part which are adapted to define a first mold cavity therebetween for molding a first part of said patient interface or patient interface component. A first material having first material characteristics, such as a first hardness, is injected into the first molding tool and into the first cavity defined thereby in order to provide the first part of the component. After said first material has been injected into the first cavity and has at least partially solidified or fully solidified the first mold cavity is opened and the first part is removed. Preferably, the molded first part is ejected or removed from the first mold part and is provided into a second cavity formed between at least a third and a fourth mold part. The third and fourth mold parts are designed and arranged so that the second mold cavity is established, as discussed above. The second cavity is larger than the first molded part so that a cavity is formed between the third mold part, the fourth mold part, and/or the first molded part.

A second material having a second material characteristic, such as a second hardness, is then fed into the second mold cavity in order to provide a second part integral with the first part. The second material is provided as a foam or foamed material. This includes that the second material is introduced or fed into the second cavity in a foamed state and/or that the second material is foamed inside the second cavity, e.g., by mans of a foaming agent. Preferably, the second material is provided or fed into the second cavity at elevated pressure and/or resulting in an elevated pressure in the second cavity, e.g. by means of the foaming agent.

Preferably, as discussed above with regard to the patient interface or patient interface component according to the present invention, the first material characteristic and the second material characteristic, such as the first hardness and the second hardness, differ from one another wherein, preferably, the first hardness is larger than the second hardness.

The mold parts are preferably arranged around a turntable. After the first part has been molded, preferably injection molded, the first molded part is removed from the first mold cavity and the first mold part is provided into the second mold cavity by turning of the turntable and by placing it in a defined position in relation to the third and fourth mold part so that it is positioned in the second cavity. Then, the second part is molded.

After the second molding step with which the second material of the second part has been provided or fed into the second cavity is finalized the tool is opened and the patient interface component can be ejected or withdrawn from the tool.

According to a further aspect of the present invention, there is provided a tool for manufacturing a patient interface or a patient interface component as discussed in the present application and/or for performing a method as discussed in the present application. Aspects of such tool have already been discussed in combination with the patient interface component or the method of the invention.

Such tool preferably comprises a first mold part and a second mold part which are adapted to define a first mold cavity therebetween. There is further provided a third mold part and a fourth mold part adapted to define a second mold cavity therebetween and/or between the first part of a patient interface component and the third and/or fourth mold part.

Preferably, the first and second mold part define walls of said first cavity whereas the third mold part, the fourth mold part and/or the first molded part define walls of said second cavity. The wall of said second cavity is preferably partly formed by or comprises the merging surface or contact region formed by the first molded part of the patient interface component.

The third mold part, the fourth mold part and/or the first molded part preferably comprise at least one pressure-flange for sealing the second cavity and preferably the first part against the third mold part and/or the fourth mold part.

Preferably, the one or more pressure flange(s) is/are designed and arranged such that it/they define(s) the merging surface on the first part of the patient interface component. Thus, the second cavity for molding the second part of the patient interface component is sealed against the first molded part so that a contact or merging surface is defined forming part of the walls of the second cavity for molding the second part of the patient interface on the first part at the merging surface.

In a preferred embodiment where at least one pressure flange is provided on the first molded part this is preferably achieved by providing a negative form of the pressure flange by the first cavity, preferably in the first mold part and/or the second mold part such that the pressure flange is molded integrally with the first molded part. The pressure flange(s) allow forming of a second cavity by sealing the first molded part, and particularly the merging surface of the first molded part against the third and or fourth mold parts, respectively.

Preferably, the first and second mold part providing the first cavity constitute an injection molding mold wherein the third and fourth mold part providing the second cavity constitute a foaming mold.

Alternatively and/or additionally to the embodiments discussed above, the pressure flange(s) is/are preferably constituted by the provision of a sealing ring, made of, e.g. silicone material. Preferably, such sealing ring, e.g. in the form of an O-ring or the like, is attached to the third and/or fourth mold part(s) by the provision of a fastening groove for attaching said ring type pressure flange to the third mold part and/or fourth mold part. This embodiment comprising one or more silicone sealing rings constituting one or more pressure flange(s) is particularly preferred for manufacturing a second molded part made of polyurethane foam.

The present invention is of particular advantage in that it provides an improved patient interface and patient interface component such as a breathing mask cushion with enhanced characteristics. In particular, the patient interface and patient interface component according to the present invention allows improved comfort for a wearer and avoids reddening and pressure marks occurring on a wearer's face. Moreover, the present invention allows the provision of special and interchangeable geometries and properties of a patient interface and a patient interface component for improved compliance with a user's physiognomy and anthropometry. The present invention particularly allows efficient and effective production of improved patient interfaces and/or components and an automated production. Moreover, optically and hygienically as well as structurally improved patient interfaces and patient interface components can be provided. In particular, individualization and comfortable wearing of such improved patient interfaces and patient interface components is allowed by the technology discussed and disclosed in this application. Preferably, the present invention additionally or alternatively allows the provision of an improved usability of the molded product, particularly by allowing the provision of a supporting structure integrally combined with a softer, foamed part.

For example the use of a first and second molded part allows the provision of a soft and comfortable material for e.g. comfortably supporting a patient interface on a users skin and of a harder material for providing improved haptic and hygienic properties, for supporting the soft comfortable material, i.e., the second portion, and/or for allowing the provision of, e.g., additional fastening means for, e.g., securing, preferably releasably and interchangeably securing, a patient interface component to a patient interface frame. A patient interface according to the present invention preferably exhibits advanced comfort to a wearer due to its light weight and the second parts material properties, which are preferably visco-elastic.

The method and tool according to the present invention particularly provide for an effective and efficient manufacturing of an improved patient interface or patient interface component having a improved characteristics. Also, the hardness and geometry of the patient interface or patient interface component may be easily adjusted or individualized without the need of an exchange of expensive tool components. Rather, e.g., a first, second, third and/or fourth mold part may be easily replaced or exchanged in order to adjust the above-listed characteristics wherein the remaining mold part(s) can be maintained. Moreover, the production of an improved patient interface or patient interface component with improved properties as regards comfort etc. is achieved in an easy and cheap manner in an automized process. Also, the present invention allows an improved production of harmonized and exchangeable modules for patient interfaces wherein the interface measures are maintained while only features relevant for the individual improvement of the patient interface or patient interface component are adjusted.

The present invention particularly and preferably has the advantageous effect that it allows the provision of an improved manufacturing process and that, e.g. during production gripping or handling sections are comolded integrally with the first and/or second molded part. These gripping or handling parts can preferably be used for demolding the patient interface component and/or for handling the patient interface component during subsequent manufacturing and/or assembly steps. The gripping or handling parts are preferably being provided on the harder, non-foamed first part. Preferably, the gripping or handling parts are adapted to be easily removed when they are not needed any more. Preferably, such gripping or handling parts comprise a predetermined breaking point zone. Additionally and/or alternatively, the gripping or handling parts are provided on the first molded part. Preferably, these gripping or handling parts, at least partly, constitute part of the contact surface. Preferably, the second material is foamed on or over the gripping or handling parts provided on the first molded part. Thus, the present invention allows an improved and automated manufacturing process. In particular, the present invention allows to handle the first part by means of a handling part, e.g. from the first cavity to the second cavity, wherein the handling part is subsequently covered by the second material.

The structure of the component of the present invention and particularly of the contact region or merging surface allows an improved filling and/or venting of the foaming tool. Moreover, the present invention preferably advantageously allows an easy and efficient production of the first part with high tolerances and low requirements or restrictions as regards the quality of the contact region or merging surface since this surface will be contacted and thus covered by the foamed second part. Furthermore, the preferred structure, e.g., a plane-, u-, cup- or elbow-shaped structure, of the merging surface of the first part allows to easily heal deficiencies in the optical appearance of the foamed second material. In particular, the preferred structures of the first part allow, e.g., to cover voids, vent structures and/or the like of the first part and/or foamed second part while at the same time allowing a secure and advanced integral connection between the first and second part.

The present invention particularly allows to manufacture one part molded with different hardness zones and/or different functionalities for use as, e.g., forehead pads (e.g., higher hardness for the attachment mechanism to the mask and lower hardness towards the patient), support portions of a headband or string, or an enhanced cushion to be attached to standard or harmonized frame interfaces.

The present invention furthermore allows to optimize the structure of a patient interface and patient interface component, respectively, based on e.g. different material characteristics. Thus, e.g., the soft, preferably visco-elastic, foam can be used for providing a cushion for in combination with a portion of higher hardness for supporting the cushion, hidden behind and covering the back of the cushion. This is also combinable with hard contact or fastening or support area(s) towards a mask frame for attachment of the component to the mask. At the same time, the production of such patient interface component is achieved in an effective and efficient manner.

According to preferred embodiments, the present invention allows to co-mold a foamed low hardness undercushion to a high hardness support, preferably in one tool. There is provided, e.g., a low hardness and viso-elastic separately molded foamed silicone undercushion and a high hardness, preferably thin, support structure. Preferably, one of the two parts, such as the foamed second part comprises coloured particles so that is has a predefined visual appearance. Preferably, the present invention allows to manufacture such multi characteristic patient interface or patient interface component in one part and in one tool. At the same time it allows to be fitted to existing, non-modified frames. The use of foam or a foamed material as the second part is of particular advantage since it also allows, although not required, the provision of, preferably small, undercuts in the connection or merging surface between the first and second part. An advantageous, effective and strong but small connection zone or merging surface or design, particularly reduced in size, is achieved.

Preferably, the tool according to the present invention is built as a tool on a turn table machine. The present invention allows to adjust the hardness/geometry of the foamed undercushion by changing only one mold half in the tool. It thus allows for anthropometrical adjustments in the tool with limited effort and/or costs.

In accordance with an aspect of the present invention there is provided a patient interface component for a breathing mask comprising a receiving opening which in the position of application of the breathing mask coincides at least with the nose and/or mouth opening region of a user of the mask, and a sealing lip which is formed from an elastomer material and which extends around the receiving opening and which in the application position fits on the surface of the face of the user of the mask. Said patient interface component may comprise zones of thickened and/or reduced cross-section.

In that way it is advantageously possible to provide a mask pad device which is distinguished by particularly high adaptability to the most widely varying individual face structures.

The patient interface according to the invention can be of such a nature that it can be fitted for example by way of a peripheral edge portion in sealing relationship to a dish-shaped or arch-shaped body in the form of a hard shell member. That makes it possible for the mask pad device to be removed from the hard shell member for cleaning, replacement, and/or adaptation purposes.

As an alternative to the measure described hereinbefore it is also possible for the patient interface component to be formed integrally with the dish-shaped or arch-shaped body. That avoids the formation of a gap region between the patient interface or interface component and the dish-shaped or arch-shaped body.

The patient interface component can be so designed that the radial cross-sections, that is to say preferably the cross-sections of the mask pad device, vary.

The above-described patient interface component forms a component part of a patient interface such as a breathing mask which, in the application position, engages over the nose and/or the mouth region of the user of a mask. It can be used in a corresponding configuration in relation to a nasal mask and also in relation to a mouth or full-face mask.

The configuration according to the invention of the cross-section of the elastomer structures can also be used in relation to a forehead contact element. Thus, in accordance with a further and also alternative concept, it is possible for forehead contact pads to be of such a configuration that the deformation characteristics thereof are imparted by foamed components.

Although the present application discusses the provision/production of a first molded part and a second molded part it is apparent for the person skilled in the art that also third and further molded parts having individual characteristics may be provided/produced.

Additional and/or alternative preferred embodiments of the present invention are directed to the following aspects.

Method of manufacturing a component of a patient interface, particularly a cushion, comprising the steps of molding a first part of the component and foaming a second part on the first part.

Method according to any one of the preceding aspects, further comprising the step of handling the first part, the second part and/or the component, wherein the first part constitutes the handling structure.

Method of producing a component of a patient interface, particularly according to any one of the preceding aspects, comprising the following steps: providing a molding tool having a first mold part and a second mold part which are adapted to define a first mold cavity there between; providing, preferably injecting, a first material into the first molding tool in order to provide a first part of the component; removing the first part from the first cavity; providing a third mold and a fourth mold part adapted to define a second mold cavity between them; inserting the first part into the second cavity; and providing a second foamed material into the second mold cavity in order to provide a foamed second part integral with the first part.

Method according to any one of the preceding aspects, further comprising the step of foaming the second material, preferably inside the second mold cavity and/or prior to providing the second material into the second mold cavity.

Method according to any one of the preceding aspects, wherein the hardness of the first part is higher than the hardness of the second part. Method according to any one of the preceding aspects, wherein the second part is visco-elastic.

Method according to any one of the preceding aspects, wherein the second material is co-molded to the first portion. Method according to any one of the preceding aspects, wherein first part removed from the first mold part and the second mold part and inserted into a third mold part and/or a fourth mold part, thereby defining, preferably in combination with the third mold part and/or the fourth mold part, a second cavity for foaming on a second part on the first part.

Method according to any one of the preceding aspects, wherein the first and/or second material comprises a color, preferably a differing color.

Method according to any one of the preceding aspects, wherein a third mold part and/or a fourth mold part are provided having at least one pressure rim structure and wherein the pressure rim structure(s) is/are sealingly pressed against the first part for defining a merging surface on the first part and/or for sealingly defining a second cavity.

Method according to any one of the preceding aspects, wherein a first mold part and/or a second mold part are provided having at least one negative pressure rim structure and wherein the molded first part comprises at least one pressure rim structure molded by the negative pressure rim structure(s) of the first and/or second part.

Method according to any one of the preceding aspects, wherein mold parts are provided having a sealing means, preferably a silicone sealing lip and/or silicone sealing ring defining at least one pressure rim which is/are sealingly pressed against the first part for defining a merging surface on the first part and/or for sealingly defining a second cavity.

Component of a patient interface, particularly a cushion, comprising a first part and a second part, wherein the second part is made of a foamed material which is foamed-on the first part. Component according to the previous aspect, wherein the first part has a hardness greater than the hardness of the second part.

Component according to and one of the previous aspects, wherein the second part is a foam, e.g., polyurethane foam or silicone foam.

Component according to any one of the previous aspects, wherein the first part is a plastic material, preferably a polymer or a thermoplastic elastomer, which is preferably elastic or hard.

Component according to any one of the previous aspects, wherein the merging or contact surface of the first part is a plane, angled or U-shaped surface structure along at least a portion of the component's circumference, and wherein the second component is foamed-on the first part such that it at least partly merges at the contact or merging surface.

Component according to any one of the previous aspects, wherein the first portion comprises a thin membrane having a thickness of preferably about 0.1 to 1 mm and more preferably of about 0.35 mm.

Component according to any one of the previous aspects, wherein the component forms a cushion or an undercushion of a patient interface and wherein the second part forms the cushion or under-cushion, and wherein the first part forms a support structure that is adapted to be connected, preferably releasably connected, to a frame of the patient interface.

Component according to any one of the previous aspects, wherein the contact area between the first and second part is a substantially plane surface and/or a surface having a substantially plane cross-section.

Component according to any one of the previous aspects, constituting a face mask cushion, a forehead pad, and/or a component of a headband for securing a device at a wearer's head.

Component according to any one of the previous aspects, comprising a pressing flange on the first part, wherein the pressing flange, preferably at least partly, defines the boundary of the merging surface.

Component according to any one of the previous aspects, manufactured according to a method according to any one of the preceding aspects.

Tool for manufacturing a component according to any one of the previous aspects and/or for performing a method according to any one of the previous aspects, comprising first mold part, a second mold part, a third mold part and a fourth mold part, wherein the first mold part and the second mold part are adapted to define a first cavity, wherein a first part is moldable in the first cavity, and wherein the third mold part, the molded first part and/or the fourth mold part are adapted to define a second cavity, and wherein one or more pressure flange(s) is are provided integrally with the third mold part, the fourth mold part and/or the molded first part.

Tool according to any one of the previous aspects, wherein pressure-flange(s) is/are adapted for sealingly contacting the third mold part, the first part and/or the fourth mold part such that the merging surface between the first part and the second part to be molded in the second cavity is defined by the pressure flange.

Tool according to any one of the previous aspects, wherein the first mold cavity is adapted to be filled with a first material in a first molding, preferably injection molding, step and wherein the second mold cavity is adapted to contain the first part and to be filled with a second foamed material.

Tool according to any one of the previous aspects, wherein the third and/or fourth mold part comprise a sealing means, preferably an O-ring or sealing lip seated in a groove provided in the third and/or fourth mold part, wherein the merging surface between the first part and the second part to be molded in the second cavity is defined by the sealing means.

A breathing mask comprising: a component according to any one of the previous aspects and/or a component manufactured by a method according to any one of the previous aspects or by a tool according to any one of the previous aspects.

Use of a tool according to any one of the previous aspects to perform a method according to any one of the previous aspects and/or for manufacturing a component according to any one of the previous aspects.

Other aspects, features, and advantages of this invention will become apparent from the following detailed description when taken in conjunction with the accompanying drawings, which are a part of this disclosure and which illustrate, by way of example, principles of the invention.

The accompanying drawings facilitate an understanding of the various embodiments of this invention. In such drawings:

FIG. 1 is a schematic three-dimensional cross-sectional view of a patient interface component of the present invention, here a patient interface cushion with a support structure;

FIG. 1*a* is an enlarged detail of FIG. 1;

Figure 5:
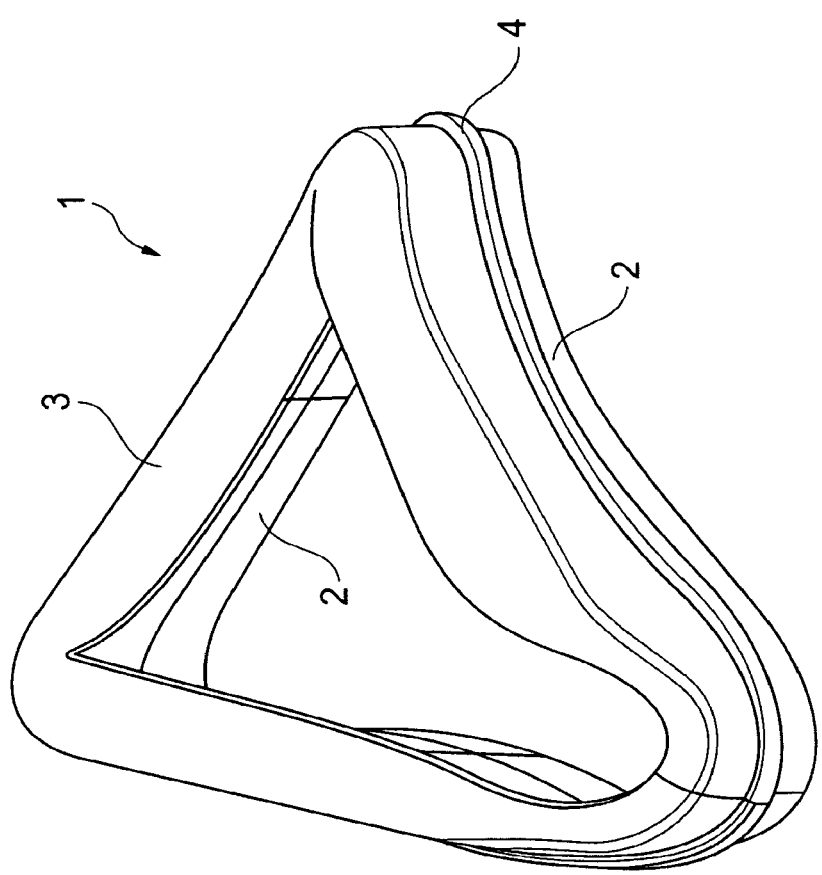
Figure 6A:
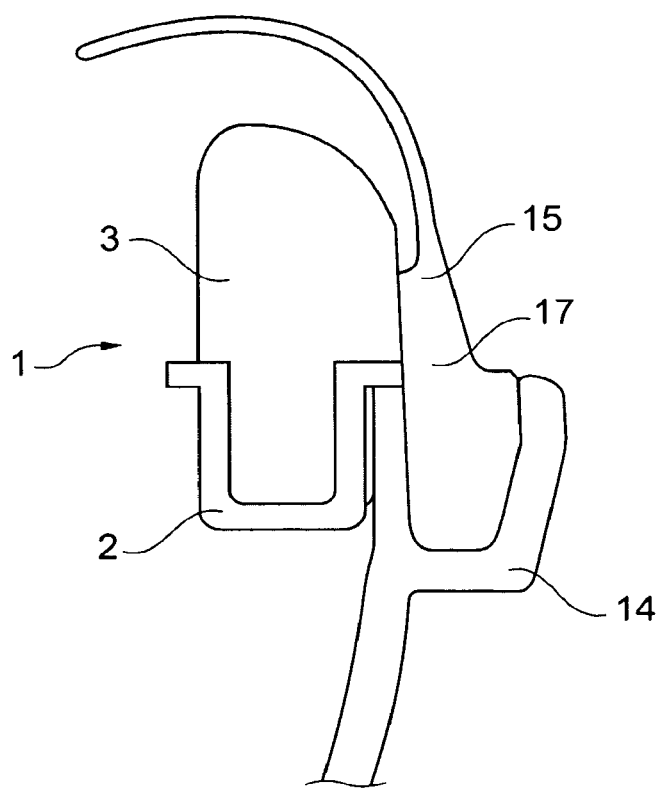
Figure 6B:
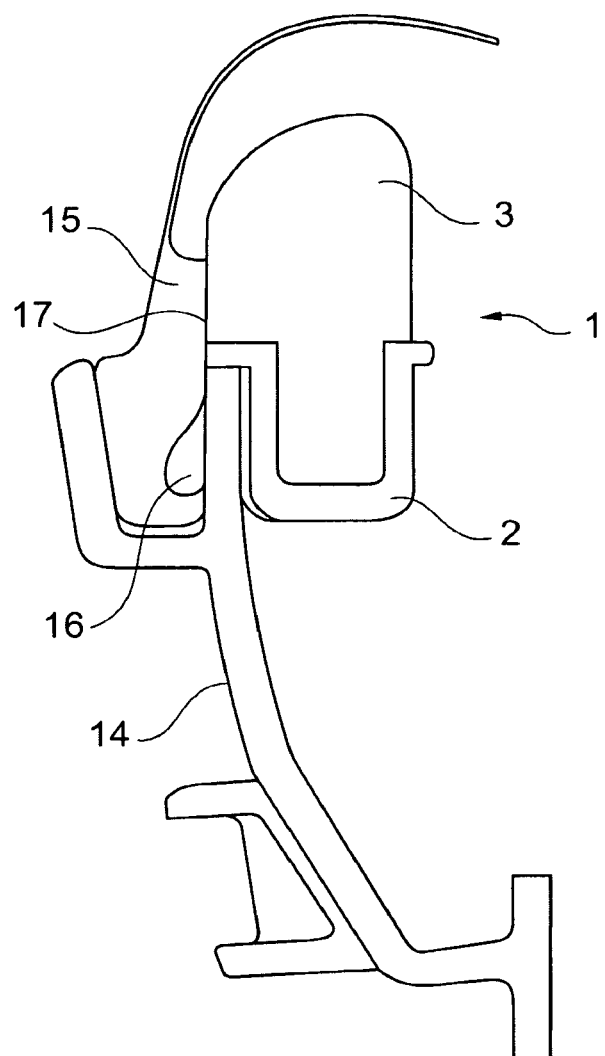
Figure 6C:
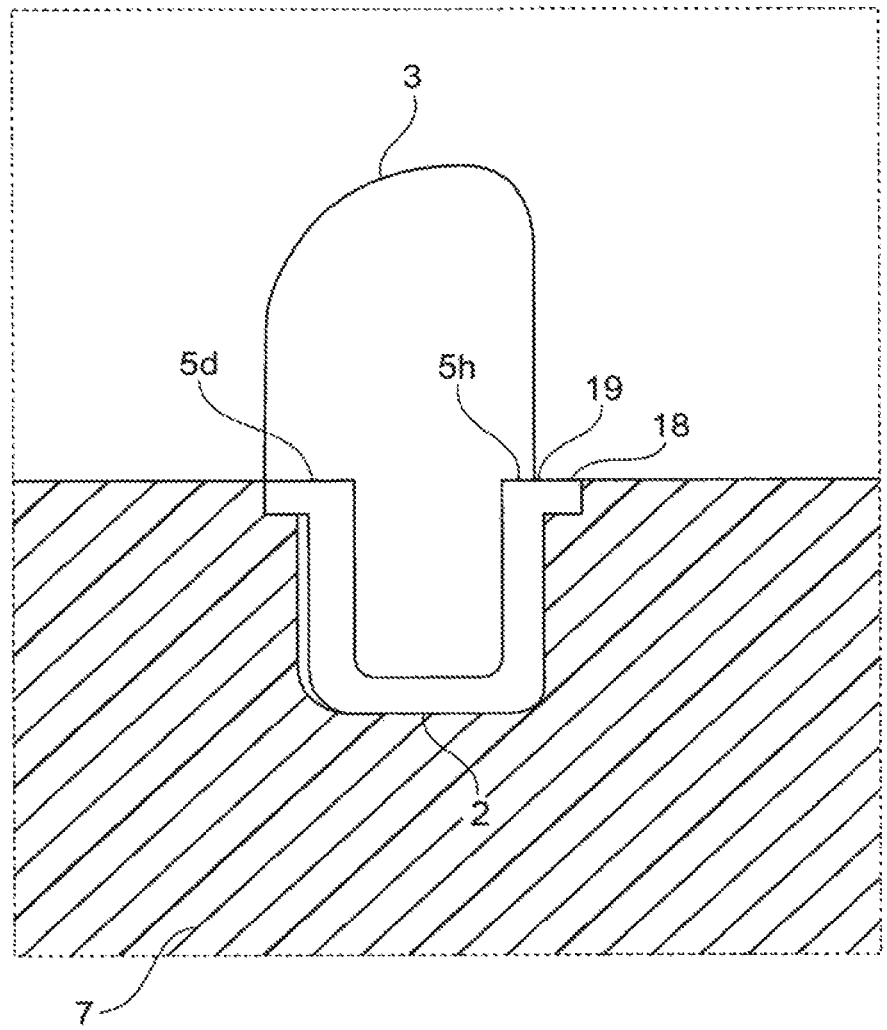
Figure 6D:
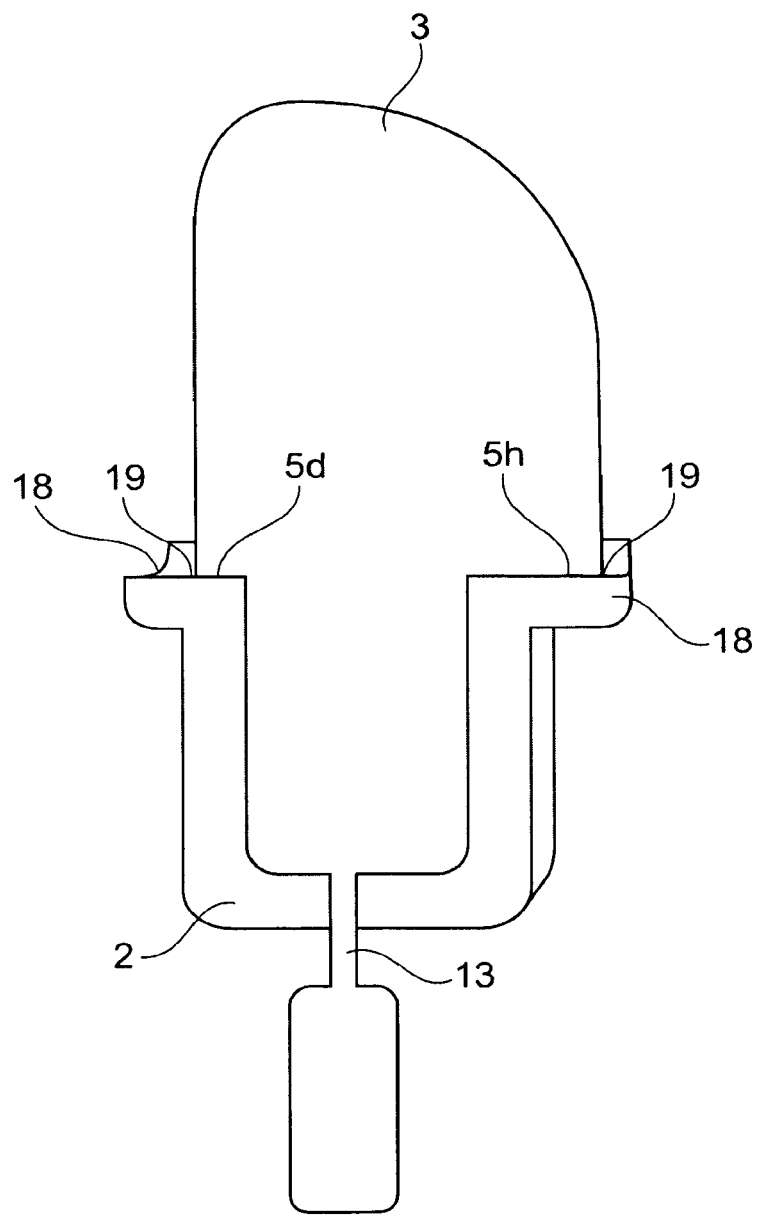

FIG. 5 shows a three-dimensional schematic view of a component according to the present invention, here a patient interface cushion with a support structure; and FIGS. 6*a* to 6*d* show preferred embodiments of components according to the present invention wherein FIGS. 6*a* and 6*b* show preferred embodiments of the component according to the present invention in combination with further structures of a patient's interface component, here a breathing mask and wherein FIGS. 6*c* and 6*d* show further preferred embodiments of the component according to the present invention.

The following description is provided in relation to several embodiments which may share common characteristics and features. It is to be understood that one or more features of any one embodiment may be combinable with one or more features of the other embodiments. In addition, each single feature or combination of features in any of the embodiments may constitute an additional embodiment.

In this specification, the word "comprising" is to be understood in its "open" sense, that is, in the sense of "including", and thus not limited to its "closed" sense, that is the sense of "consisting of". A corresponding meaning is to be attributed to the corresponding words "comprise", "comprised" and "comprises" where they appear.

Figure 1:
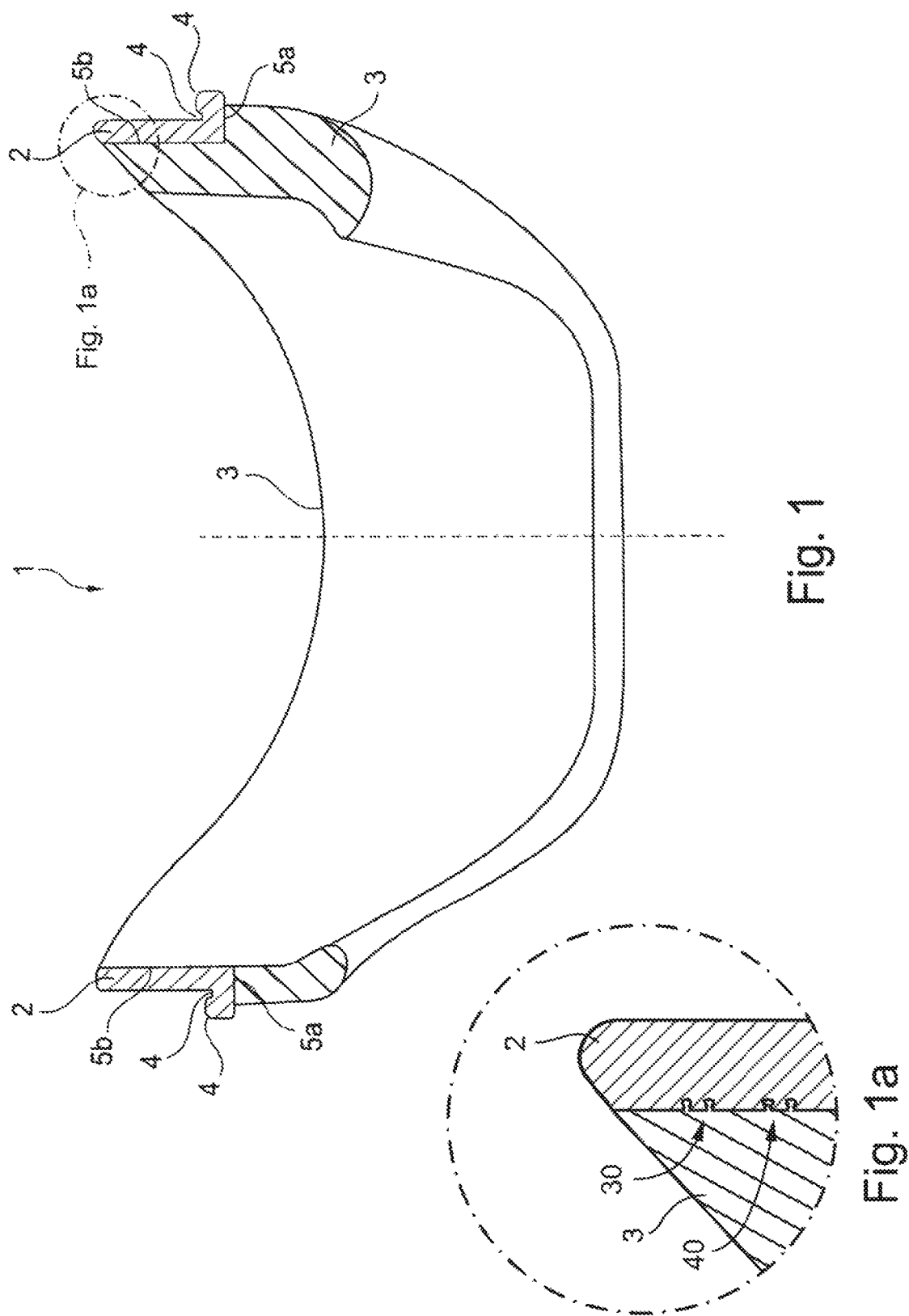

In accordance with the present invention, FIG. 1 shows a three-dimensional schematic cross-sectional view of a patient interface structure or component 1 according to the present invention. The patient interface structure comprises a first part 2 and a second part 3 wherein the second part 3 is made of a foamed material which is foamed on the first part 2. The first part 2 and the second part 3 integrally merge at a merging surface 5 (5 *a*, 5 *b*) which constitutes the contact area between the first part 2 and the second part 3. The contact surface of the first part 2 may comprise bores 30 and/or cavities 40 which are at least partly filled by the second part 3 when foaming the second part on the first part. According to the embodiment shown in FIG. 1, the first part 2 constitutes a frame or a support portion wherein the second part 3 constitutes a cushion or under cushion portion of the patient interface. The patient interface component 1 according to the present invention, and preferably its first portion 2, preferably comprises structural fastening or connection means 4 for connecting the patient interface component 1 to a patient interface structure such as a breathing mask or a mask frame.

The second part 3 is made of or comprises a foamed material or a foam material, preferably silicone foam or polyurethane foam. The first part 2 preferably is or comprises a plastic material such as a polymer, or thermoplastic elastomer. Preferably, the first part 2 has a greater hardness than the second part 3. Furthermore, preferably, the material of the second part 3 has greater elasticity and/or viscoelasticity than the material of the first part 2.

Figure 2:
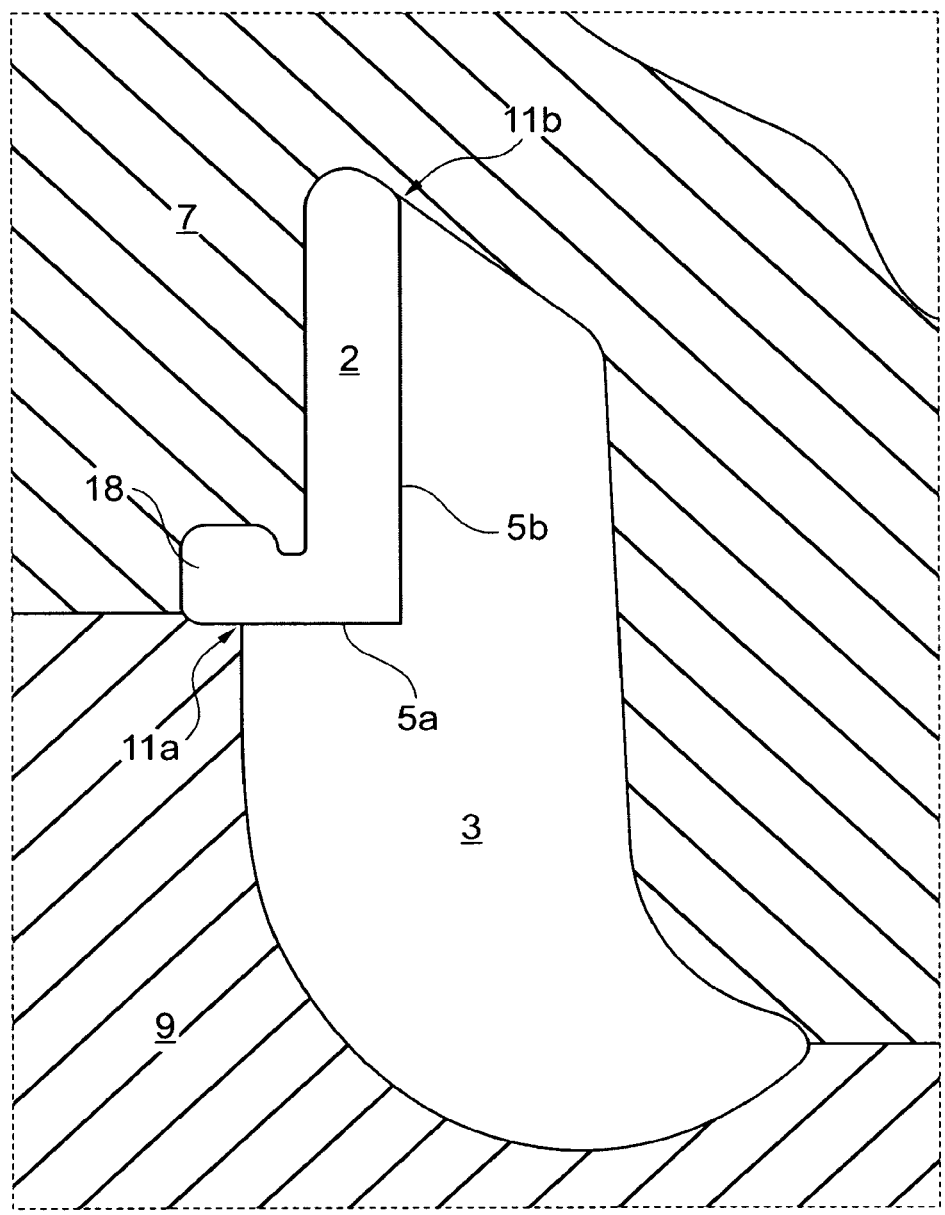
FIG. 2 shows a schematic view of the cross-section of the component according to in FIG. 1.

FIG. 2 shows a schematic cross-sectional view of the cross-section shown on the right hand side in FIG. 1. As shown in FIGS. 1 and 2 the contact or merging surface 5 between the first part 2 and the second part 3 comprises two distinct surface portions 5a, 5b which are inclined toward to another by an angle, preferably of about 90°, and form a contiguous contact zone or merging surface 5.

During manufacturing, the first part (first molded part) 2 is molded in a first mold cavity between a first mold part (not shown) and a second mold part (not shown). After molding of the first part 2, the first molded part 2 is removed from the mold and is inserted into a second cavity formed or to be formed between a third mold part 7 and a fourth mold part 9. Preferably, the third mold part 7 and the fourth mold part 9 define a second cavity between them. Preferably, the first molded part 2 is located in said second cavity wherein the second cavity is larger than the first molded part 2. Thus, once the first molded part 2 is inserted into the cavity formed between the third and fourth mold part and the third and fourth mold parts are closed still a cavity remains. This remaining cavity is also referred to a second cavity herein. Preferably, a part of the wall of said second cavity is defined by the first part 2 contained between the third mold part 7 and/or the fourth mold part 9. Said second cavity being for molding the second part 3.

The second cavity and thus the second part 3 preferably has varying dimensions and measures, particularly along the circumference of the patient interface, and/or the contact surface 5 preferably has varying dimensions and measures, particularly along the circumference of the patient interface. This is shown, e.g. in FIG. 1.

Generally, it is to be noted that the third mold part, the fourth mold part or any further mold parts according to the present invention can be constituted by one, two or more individual parts. For example, in the embodiment shown in FIG. 2, the fourth mold part 9 can be defined by two mold parts 9a and 9b (not shown).

The fourth mold part 9 and/or the third mold part 7 comprise a pressure-flange 11 for sealingly contacting the first molded part 2 contained in the second cavity between the third mold part 7 and the fourth mold part 9.

Preferably, the pressure flange(s) is(are) designed and arranged such that it (they) defines (define) the contact of merging surface 5 on the first part 2 of the patient interface component 1. Thus, the second cavity for molding the second part 3 of the patient interface component 1 is sealed against the first molded part so that a contact or merging surface 5 is defined forming part of the walls of the second cavity for molding the second part 3 of the patient interface 1.

Additionally or alternatively, at least one pressure flange 11, and preferably two pressure flanges 11 (11a, 11b) is/are provided on the third mold part 7, the fourth mold part 9 and/or the first part 2. In a preferred embodiment, where a pressure flange 11 is provided on the first part 2 this is preferably achieved by providing a negative form of the pressure flange 11 in the first mold part and/or the second mold part such that the pressure flange 11 is molded integrally with the first part 2. The pressure flange(s) 11 allow forming of a second cavity by sealing the first part 2, and particularly the merging surface 5 of the first part 2 against the third and/or fourth mold part.

The second cavity is then filled with a foamed material for forming the second part 3. Preferably, a second material and/or a foaming agent are provided into the second cavity such that the second cavity is filled with a foamed or foaming material that contacts and merges with the first part 2 at merging or contact surface 5.

The contact or merging surface 5 can be a surface lying in one plane, or, as shown, e.g., in FIGS. 1 and 2, a surface having surface portions lying in two or more planes. In FIG. 2, a third mold art 7 and a fourth mold part 9 have been schematically and exemplarily indicated. The third mold half 7 is shown to comprise a pressure flange 11, preferably two pressure flanges 11a and 11b, which sealingly contact(s) the first part 2. Each pressure flange 11 is arranged and designed such that it defines a, or part of a, contact or merging surface 5. Preferably, each pressure flange 11 is of a continuous structure such that there is defined an enclosed, clearly defined individual contact or merging surface 5 on the first part 2. Preferably, the pressure flange(s) have a continuous, ring like shape so that a continuous boundary of the merging surface 5 is defined. This can also be achieved by providing two or more pressure flanges which supplement one another to define such merging surface. Preferably, merging surface 5 is of ring like shape, and is preferably defined by two ring like pressure flanges.

Figure 3:
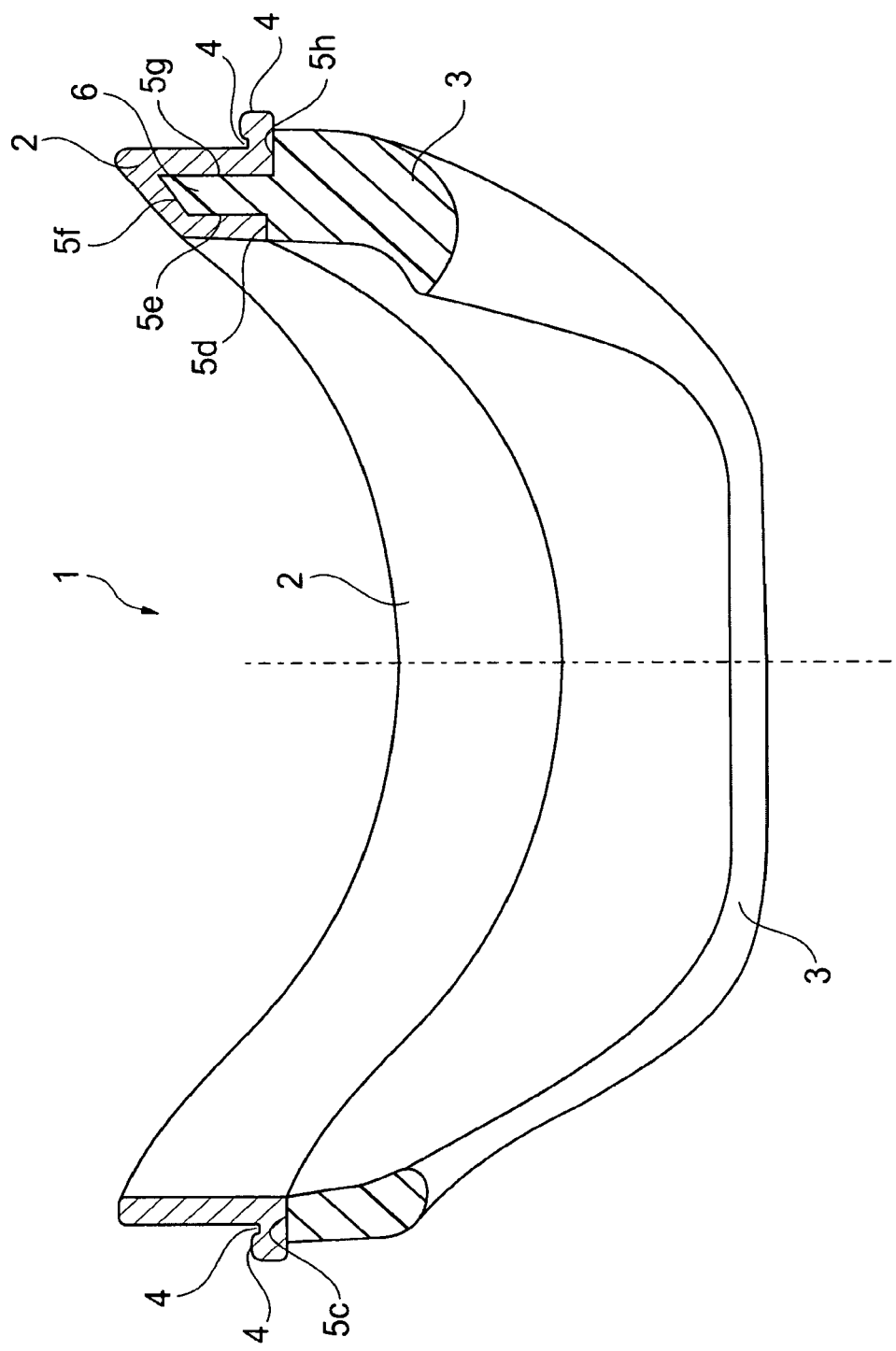
FIG. 3 shows a schematic three-dimensional cross-sectional view of another embodiment of a patient interface component according to the present invention, here a patient interface cushion with a support structure.

Preferably there will be provided two endless or loop-like pressure flanges 11a and 11b extending all around the circumference of a molded first part 2 and define between them the contact or merging surface 5. This is of particular advantage for molding a patient interface components as shown in FIG. 1, 3, or 5 (discussed below) which are of generally circular, oval or triangular but generally ring-like shape. Alternatively, the pressure rim or pressure flange has a ring-like structure enclosing, inside said structure, the merging surface 5. In such case, the patient interface component does not need to be generally ring-shaped, e.g., in case of a forehead cushion or a headband support.

Alternatively, pressure rim or pressure flange 11 can also be provided on the fourth mold half 9.

The pressure flange or pressure rim 11 preferably seals the second mold cavity against the first part 2. Thus, the second mold cavity is defined by the contact or merging surface 5 of the first part 2 and surface portions of the first mold part 7 and/or the third mold part 9. Preferably, at least one of the pressure flanges has an interruption, particularly in order to provide, e.g., a sprue or a venting structure.

Figure 4:
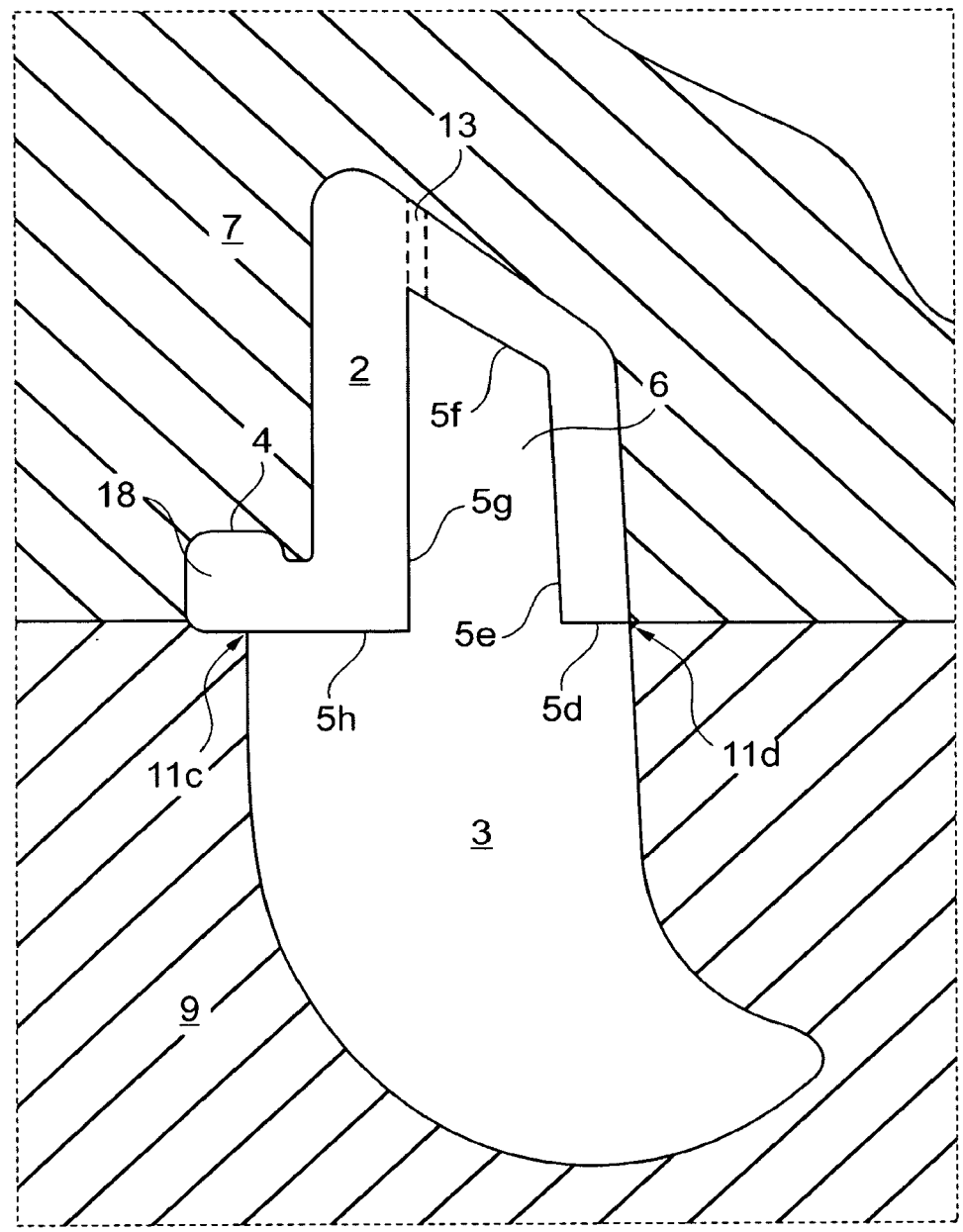
FIG. 4 shows a schematic view of the cross-section of the component according to FIG. 3.

The embodiment shown in FIGS. 3 and 4 basically corresponds to the embodiment discussed above with regard to FIGS. 1 and 2. It is thus referred to the above discussion. The embodiment shown in FIGS. 3 and 4 differs from the embodiment discussed above e.g. with regard to the structure and design of the contact surface 5. As can be seen in the cross-sectional view according to FIG. 3, the shape and structure of the contact surface 5 may vary along its length, here along the circumference of the patient interface component. As shown on the left hand side in FIG. 3, a contact surface 5 (here referred to as 5c) is a plane surface. Compared thereto, on the right hand side in FIG. 3 a contact surface 5 comprises different surface sections referred to as 5d, 5e, 5f, 5g, 5h. In its general structure, the contact or merging surface 5 on the right hand side of FIG. 3 has a U-shaped structure with flange portions 5d, 5h at the opening of the U. In other words, contact surface 5 on the right hand side of the embodiment shown in FIG. 3 comprises a depression or groove 6 defined by surface portions 5e, 5f and 5g.

As shown in FIG. 4, such structure or merging surface 5 can be manufactured by using a tool comprising a third mold half 7 and a fourth mold half 9 wherein the third mold half 7 comprises a pressure rim 11d for sealingly contacting the first molded part 2 and defining one border or boundary of contact surface 5. Fourth mold half 9 comprises a second pressure rim 11c for sealingly contacting the first part 2 and defining a second border or boundary of contact surface 5.

The discussions provided above with regard to the definition of the second cavity or the structure of the tool etc. also apply to the embodiment shown in FIGS. 3 and 4.

According to the present invention, the pressure rim(s) 11 provided on one or more of the mold halves and/or the first part 2 is/are a thin, preferably sharp rim or protrusion. Pressure flange(s) 11 is/are pressed against and into the material of the first part 2 and/or the mold halves in order to sealingly define the second cavity as discussed above. Pressure flange(s) 11 is/are either pressed against and into the molded first part 2 by pressing a mold part 9 and thus the pressure flange(s) against the first part 2. Additionally or alternatively, one or more pressure flange(s) 11 sealingly abut(s) the first part 2 since it/they already form part of the third mold part 7 in which the first part 2 is inserted.

Preferably, the pressure flange protrudes from the remainder of the mold halves surfaces. Preferably, the pressure rim has a tapered or pointed configuration.

The shape and arrangement of the contact or merging surface is preferably adapted to apply certain structural features being advantageous for the molding process, the tool design and/or the final product, e.g. a patient interface component. According to a preferred embodiment, the design of the merging surface 5 changes along the circumference of the first part 2, preferably in order to exhibit certain functionalities and advantages discussed herein at predefined positions of a wearer's face. For example, a contact or merging surface 5 comprising two angled surface components, such as surface portions 5a and 5b shown in FIGS. 1 and 2, allows a clear positioning of the second part with respect to the first part and thus with respect to the remainder of the patient interface. For example, according to a preferred embodiment, the first part 2 defines a connection structure for connecting the second part 3, preferably an under-cushion of a patient interface, to the face mask thereby facilitating guidance, connectability, exchangeability, individualizeability etc. of the patient interface component and thus the patient interface according to the present invention. This preferably allows a decoupling of the softer second part 3 from the mask body by means of the first molded part 2 serving as an adapter.

Alternatively or additionally, the design of the contact or merging surface 5 is chosen to influence the hardness, elasticity and support functionality of the patient interface component and particularly of the foamed second part 3, preferably constituting a patient interface under-cushion.

Furthermore, contact surface shapes as shown in FIG. 2 or FIG. 4 allow a foaming of the second part 3 onto the first part 2 such that any potentially hygienically and/or optically deteriorated parts or surfaces of the foamed second part 3 are hidden and sealed by the merging surface 5, e.g. in the corner of merging surface portions 5a and 5b according to FIG. 2 or in the recess 6 formed by surface portions 5f, 5g, 5h according to FIG. 4. Preferably, the mold parts constituting the second mold cavity for forming the foamed second part 3 are designed and arranged such, e.g. with regard to gravity, that any potentially deteriorated and/or visually or hygienically disadvantageous part of the foamed second part and/or the merging surface 5 is covered or sealed as discussed above.

According to a further preferred embodiment of the present invention, venting structures 13 are formed into the first molded part 2, preferably while molding the first part 2. Preferably, the respective venting structures or channels are provided in or at the contact or merging surface 5 and, preferably, in or at those portions discussed above as being suitable for hiding and sealing certain parts of the second part. E.g., in FIG. 4, a venting structure 13 is exemplary depicted as being provided in merging surface portion 5f in groove 6.

Alternatively and/or additionally to the embodiments discussed above, pressure flange 11 can also be constituted by the provision of a sealing means or sealing ring, made of, e.g. silicone material. Preferably, such sealing ring, preferably in the form of, e.g. a sealing lip, a flexible sealing means, an O-ring or the like, is attached to the third and/or fourth mold part(s) by the provision of a fastening groove for attaching said sealing means to the third mold part and/or fourth mold part. This embodiment comprising one or more silicone sealing structures or rings constituting pressure flange(s) is particularly preferred for manufacturing a second part 3 made of polyurethane foam.

According to a preferred embodiment, the pressure rim(s) are provided on the first part 2 for sealingly contacting the fourth mold part 9. In this case, the pressure flange(s) 11 is/are part of the molded first part 2. This is preferably achieved by providing a first and/or second groove or recess of the negative shape of the pressure flange 11 in the first mold part 7 and/or the second mold part so that the molded first part integrally comprises the pressure flange 11.

According to a preferred embodiment, the first molded part 2 is designed such that it comprises a membrane forming a sealing lip for sealingly contacting a user's skin.

FIG. 6a shows a component according to the present invention comprising a first molded part 2 and a second foamed part 3 being attached to a mask frame 14. Further attached to mask frame 14 is a membrane 15 which extends over second foamed part 3. Preferably, membrane 15 and/or component 1 (comprising first molded part 2 and second part 3) are releasably attached to mask frame 14 by means of respective fastening means (not shown). Preferably, membrane 15 extends over component 1 so that when the breathing mask is worn by a patient, membrane 15 contacts the user's skin wherein the mask is supported on the user's skin by means of component 1, i.e., foamed second part 3 constituting a mask cushion or undercushion which is held or supported by means of first molded part 2 which is connected to the breathing mask via mask frame 14. Preferably, membrane 15 is a silicone membrane.

FIG. 6b shows the use of a component 1 according to the present invention similar to the embodiment discussed with regard to FIG. 6a. As with the embodiment shown in FIG. 6a, membrane 15 is releasably attached to frame 14 wherein membrane 15 supports, covers, protects, and/or extends over component 1. Contrary to the embodiment shown in FIG. 6a, membrane 15 according to FIG. 6b comprises a cavity or recess 16 which preferably allows a good gliding and dampening function of membrane 15. Membrane 15 also comprises an abutment surface 17 which preferably supportingly abuts against component 1.

FIG. 6c shows a first part 2 inserted in third mold half 7. Mold part 2 as a generally U-shaped contour in the cross-section according to FIG. 6c, wherein the ends of the generally U-shaped contour of first element 2 are bent. Thus, corresponding to the embodiment shown and discussed with regard to FIG. 4, merging surface 5d and 5h are formed. Preferably, at least one bent or bent end of the generally U-shaped contour of first element 2 extends beyond a second foam part 3. A respective extension 18 is indicated in FIG. 6c. It will be apparent for the person skilled in the art that a respective extension can be formed on both ends of U-shaped contour of first element 2. Additionally and/or alternatively, a respective configuration can also be achieved with the embodiment shown in FIG. 7.

Extension 18 provides an additional advantageous possibility to apply a pressure rim (not shown in FIG. 6c) to define merging surface 5h and to prevent foam or second foamed part 3 to extend beyond boundary point/line 19.

With regard to gravity, when foaming second part 3 onto first part 2, first part 2 is arranged in the upper part of the tool whereas second foamed part 3 constitutes the lower part of the tool. Accordingly, the foam constituting of building second foamed part 3 will build up from the lower part of the cavity (which is the upper end of second foamed part 3 according to FIG. 6c) and be build up or filled up to first molded part 2.

As already indicated, first part 2 and/or second part 3 preferably comprise the same or different colour pigments allowing to indicate, e.g., different sizes and/or structural features of component 1.

The preferred embodiment according to FIG. 6d generally corresponds to the one discussed with regard to FIG. 6c wherein extensions 18 are provided on both ends of first parts 2 generally U-shaped contour. In addition, second part 2 comprises venting structures 13 which can be used for venting and/or filling of the second cavity for molding or foaming the second foamed part 3.

The present invention, particularly the method according to the present invention and the tool according to the present invention allow an advantageous foaming of a second part on a first part which has been proven to be either not possible or disadvantageous as discussed in the introductory portion of the specification. In this context, it is particularly to be noted that material to be foamed or foamed material is generally a liquid material having a low viscosity and is formed under pressure so that the achievement of a reliable easy, efficient and effective seal in accordance with the present invention is of great advantage. Such material to be foamed or foamed material furthermore generally exhibits sticky characteristics. Thus, the present invention it is of advantage in order to avoid the production of deficient parts or clogging of the mold parts. Thus, according to the present invention, there is no need to cut off or stamp out certain parts of the foamed material or to clean any remaining surfaces of the mold parts or the first molded part.

The present invention moreover or alternatively allows improved connection and/or mounting of the foamed second part. The foaming of the second part on the first molded part preferably provides improved tolerances and/or sealing properties of the molded first and/or part against the remaining mask components and/or a patient's face. Preferably, the present invention additionally or alternatively allows selective stiffening or reinforcing of the foamed second part by designing the first molded part and/or the merging surface accordingly. This leads to improved sealing properties of a patient interface component in line with the present invention. Correspondingly, the present invention allows improved automating of production and particularly of the deforming of the foamed part and subsequent manufacturing steps such as flash removing. Preferably, also the filling and/or venting of the second cavity is improved. The present invention preferably alternatively or additionally allows the application of colour, such as coloured codes, to the molded parts, such as the foamed second part. Correspondingly, automation of the assembly and hiding of defects is allowed.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from sleep disordered breathing such as OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A patient interface for the therapeutic administration of breathable gas for sleep disordered breathing, comprising:
   a first part comprising a support structure for the patient interface; and
   a second part comprising 1) a mask cushion configured to, in use, seal with a patient's airway, or 2) an undercushion configured to, in use, support a seal element in sealing contact with the patient's airway,
   wherein the second part comprises a foamed material which is foamed-on the first part such that the first part and the second part are formed integrally with one another, and
   wherein a surface of the first part includes non-through holes formed therein which are at least partly filled by the second part when the second part is foamed-on the first part so that the first part and the second part integrally merge at a merging or contact surface, without the second part substantially surrounding the first part and without positive locking.

2. A patient interface according to claim 1, wherein the second part is a polyurethane foam or silicone foam and/or wherein the first part comprises plastic.

3. A patient interface according to claim 2, wherein the plastic of the first part is a polymer or a thermoplastic elastomer.

4. A patient interface according to claim 3, wherein the plastic of the first part has a higher hardness as compared to a hardness of the second part.

5. A patient interface according to claim 1, wherein the merging or contact surface is a plane, angled or U-shaped surface structure along at least a portion of the mask cushion's or undercushion's circumference.

6. A patient interface according to claim 1, wherein the second part comprises the mask cushion, and the mask cushion constitutes a face mask cushion.

7. A patient interface according to claim 1, wherein the first part comprises the seal element, and the seal element comprises a membrane configured to sealingly contact the patient's skin.

8. A patient interface according to claim 7, wherein the second part comprises the undercushion, and the undercushion is arranged to be covered by the membrane and to provide support to the membrane when the membrane contacts the patient's skin.

9. A patient interface according to claim 1, wherein the first part and the second part are co-molded.

10. The patient interface according to claim 1, wherein the merging or contact surface comprises a plurality of surface portions including first and second surface portions, the first surface portion and the second surface portion being angled with respect to one another to form an elbow shape in cross-section.

11. The patient interface according to claim 1, further comprising a mask frame attached to the first part.

12. The patient interface according to claim 1, wherein the merging or contact surface forms only a plane surface, in cross-section.

13. The patient interface according to claim 1, wherein, in a cross-sectional view, the merging or contact surface comprises a plurality of surface portions forming a U-shaped structure.

14. The patient interface according to claim 13, wherein the plurality of surface portions further comprise flange portions at the opening of the U shape.

15. The patient interface according to claim 1, wherein, in a cross-sectional view, a shape of the merging or contact surface varies along a circumference of the patient interface.

16. The patient interface according to claim 15, wherein at a first location along the circumference, the merging or contact surface forms only a plane surface in cross-section, and at a second location along the circumference the merging or contact surface comprises a plurality of surface portions forming a U-shaped structure in cross-section.

17. The patient interface according to claim 1, wherein the first part is elongate, in a cross-sectional view of the patient interface.

18. The patient interface according to claim 17, wherein the second part is elongate, in the cross-sectional view.

19. The patient interface according to claim 18, wherein, in the cross-sectional view, a width of the second part is smaller than a height of the second part.

20. A patient interface according to claim 1, wherein the merging or contact surface constitutes a contact area between the first part and the second part.

21. A patient interface according to claim 1, wherein the first part and the second part integrally merge at the merging or contact surface without the first part and the second part forming a form closure arrangement.

22. A patient interface according to claim 1, wherein the first part does not form a core with the second part substantially surrounding the first part.

23. A patient interface for the therapeutic administration of breathable gas for sleep disordered breathing, comprising:
a first part; and
a second part,
wherein the second part comprises a foamed material which is foamed-on the first part such that the first part and the second part are co-molded and thereby formed integrally with one another,
wherein a surface of the first part includes non-through holes formed therein which are at least partly filled by the second part when the second part is foamed-on the first part so that the first part and the second part integrally merge at a merging or contact surface into one integral surface without the second part substantially surrounding the first part and without positive locking,
wherein 1) the first part comprises a membrane configured to, in use, sealingly contact a patient'S skin and the second part comprises an undercushion arranged to, in use, be covered by the membrane and to provide support to the membrane when the membrane contacts the patient's skin, or 2) the second part comprises a mask cushion configured to, in use, seal with a patient's airway,
wherein the merging or contact surface comprises a plurality of surface portions including first and second surface portions, the first surface portion and the second surface portion being angled with respect to one another, and
wherein the second part is a polyurethane foam or silicone foam and/or wherein the first part comprises plastic.

24. A patient interface according to claim 23, wherein the merging or contact surface is a plane, angled or U-shaped surface structure along at least a portion of a circumference of the patient interface.

25. A patient interface according to claim 23, wherein the first part comprises the membrane configured to, in use, sealingly contact the patient's skin and the second part comprises the undercushion arranged to, in use, be covered by the membrane and to provide support to the membrane when the membrane contacts the patient's skin.

26. A patient interface according to claim 23, wherein the second part comprises the mask cushion configured to, in use, seal with the patient's airway.

27. A patient interface according to claim 23, wherein the first surface portion and the second surface portion form an elbow shape in cross-section.

28. A patient interface according to claim 23, wherein, in a cross-sectional view of the patient interface, the plurality of surface portions form a U-shaped structure.

29. The patient interface according to claim 28, wherein the plurality of surface portions further comprise flange portions at the opening of the U shape.

30. The patient interface according to claim 29, wherein, in the cross-sectional view of the patient interface, a shape of the merging or contact surface varies along a circumference of the patient interface.

31. A patient interface according to claim 23, wherein the merging or contact surface constitutes a contact area between the first part and the second part.

32. A patient interface according to claim 23, wherein the first part and the second part integrally merge at the merging or contact surface without the first part and the second part forming a form closure arrangement.

33. A patient interface according to claim 23, wherein the first part does not form a core with the second part substantially surrounding the first part.

* * * * *